United States Patent [19]

DeAngelis

[11] 4,116,836
[45] Sep. 26, 1978

[54] CHROMATOGRAPHIC COLUMN

[75] Inventor: William M. DeAngelis, Wilton, Conn.

[73] Assignees: Henry Allen, Mamaroneck; Charles J. Garbarini, Jr., New York, both of N.Y.

[21] Appl. No.: 773,325

[22] Filed: Mar. 1, 1977

[51] Int. Cl.² ............................................. B01D 15/08
[52] U.S. Cl. .................................... 210/198 C; 55/386
[58] Field of Search ............. 210/31 C, 198 C; 55/67, 55/386

[56] References Cited

U.S. PATENT DOCUMENTS

| 3,116,161 | 12/1963 | Purnell | 55/386 X |
| 3,149,941 | 9/1964 | Barnitz et al. | 55/386 |
| 3,319,403 | 5/1967 | Rose et al. | 55/386 |
| 3,796,657 | 3/1974 | Pretorius et al. | 55/386 X |
| 3,856,681 | 12/1974 | Huber | 55/386 |

*Primary Examiner*—John Adee
*Attorney, Agent, or Firm*—Barry Kramer

[57] ABSTRACT

A monolithic glass construction having a continuous passageway formed therethrough packed with chromatographic packing material is used as a chromatographic column. The monolithic construction enables the column to be formed of the longest practical length and smallest practical diameter to increase the efficiency of the column, while also providing a durable column. Quick-connect and disconnect couplings to a gas feed and analysis device are mounted on the monolithic construction.

22 Claims, 10 Drawing Figures

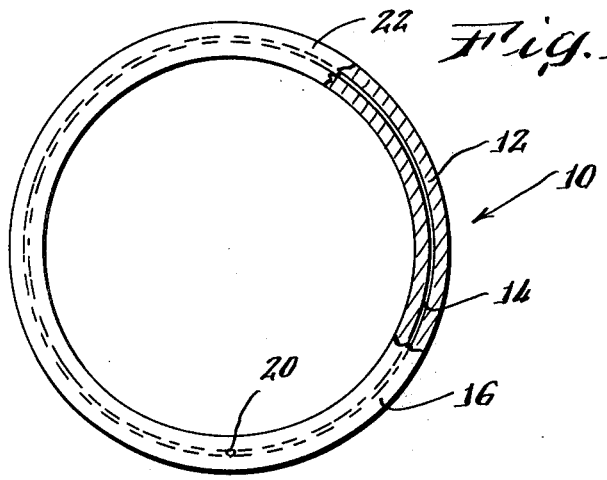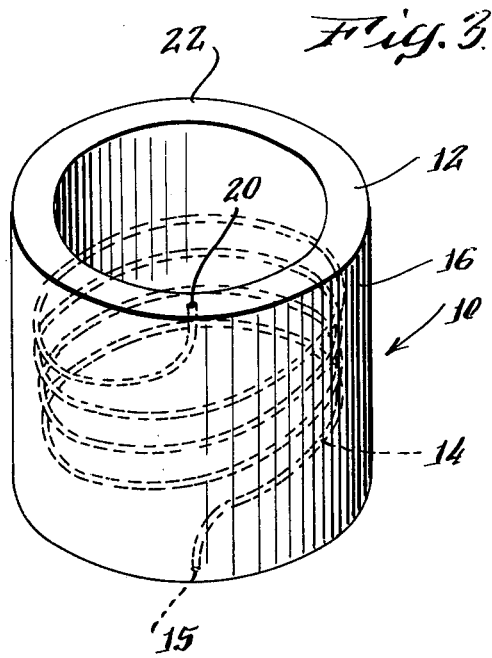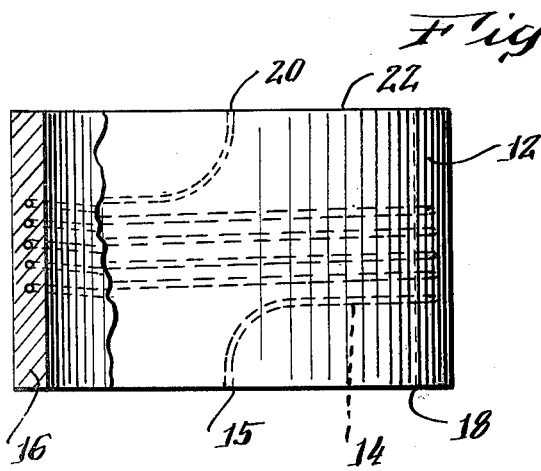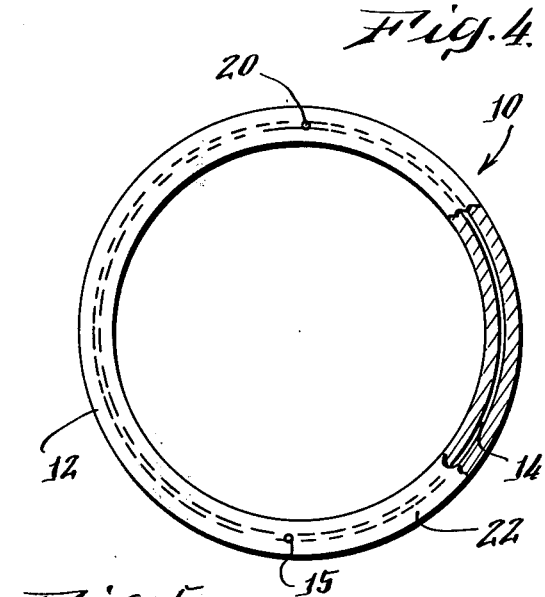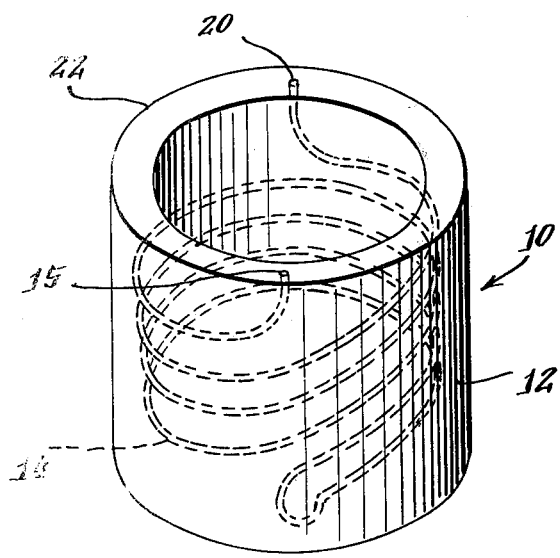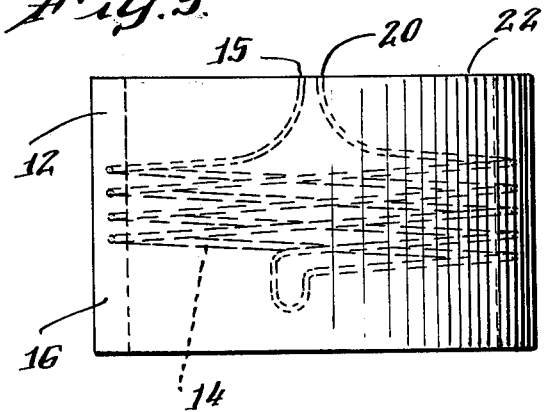

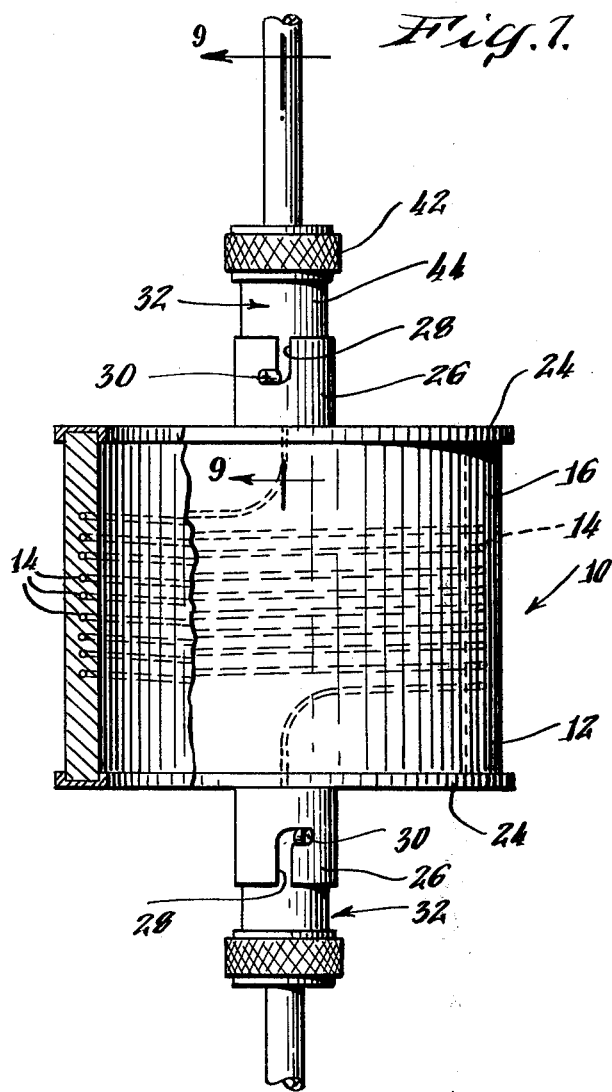
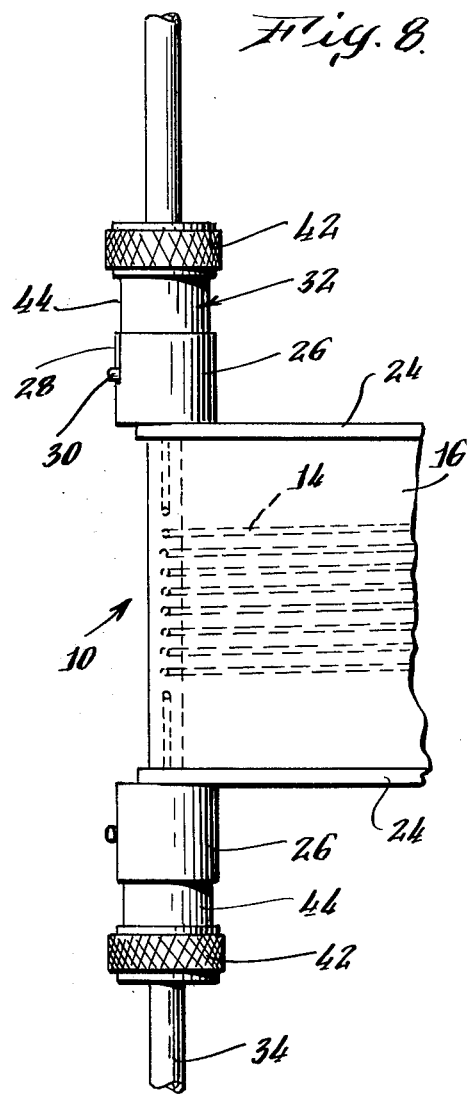
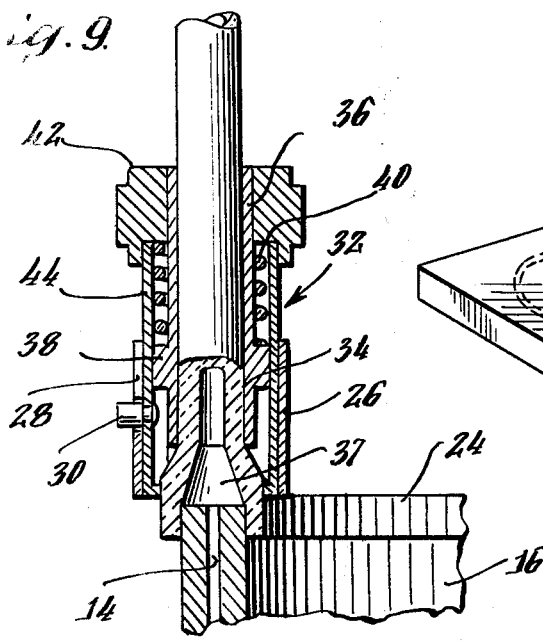
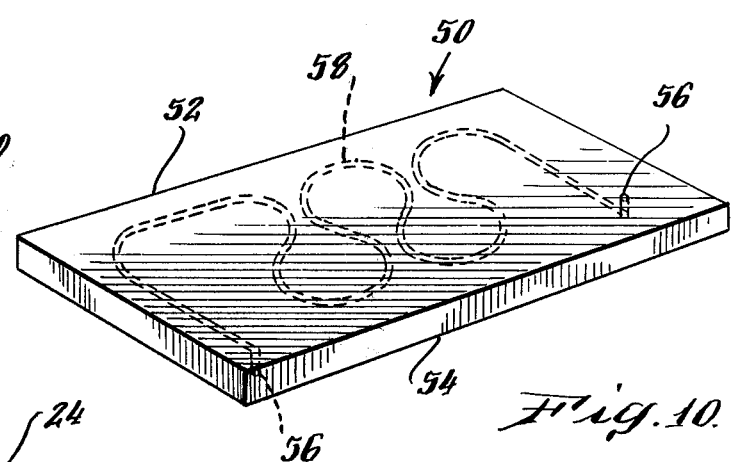

CHROMATOGRAPHIC COLUMN

BACKGROUND OF THE INVENTION

1. Field of the Invention

This invention relates to the field of chromatography and more particularly, to improvements in chromatographic columns used as an analytical tool for the separation, identification, and quantitative determination of mixtures of volatile compounds (gases and liquids).

2. Description of the Prior Art

Chromatography, in all forms, is a technique used to separate a mixture of compounds or elements into the components thereof. All chromatographic processes consist of two basic segments: a mobile phase and an immobile phase. The mobile phase moves through a tube, called a column containing the immobile phase, and the sample to be separated into its basic components is injected in the mobile phase into the column. As the sample is swept forward by the mobile phase, the sample components are either adsorbed on the surface of the immobile phase (if the immobile phase is a solid) or dissolved in the immobile phase (if it is a liquid). As the mobile phase passes into the column behind the sample, components of the sample desorb back into it. This adsorption-desorption process continues throughout the length of the column. Each sample component in the mobile phase moves at a different rate through the column depending on its attraction for the immobile phase. The components therefore separate as they pass through the column and emerge at the other end of the column at different times.

In gas chromatography, the sample to be analyzed is comprised of volatile components which are carried through the column in a gaseous state by an inert mobile phase, called the carrier gas. The immobile phase is either a solid in the form of uniform particles or a thin film on either uniform particles or the column walls.

Therefore, under proper conditions, various components of the gas sample are spacially separated by the process of selective adsorption and desorption so that the separated gas constituents issue from the end of the column in sequential order corresponding to their relative volatility, their molecular weight, or other property affecting the degree of adsorption on the immobile phase or packing material in the column. Conventionally, as the separated gases emerge they are passed through a suitable detector element which measures a property of the gas indicative of the character and amount present.

The immobile phase or packing most commonly used in chromatographic columns comprise diatomaceous earth, alumina, glass beads, fluorocarbons, and silica gel. Conventionally the packing, whatever form is chosen for a particular chromatographic column, is poured into the column in granular form and compacted therein by vibration, tamping or the like. An inert gas, such as helium, argon or nitrogen acts as the carrier gas for the sample and flows continuously through the instrument. The use of an inert mobile carrier gas assures that the carrier gas does not react with either the sample or the immobile phase.

Samples are introduced into the carrier gas either as a liquid or a gas. Usually, liquid samples in the order of 10 microliters or less are injected rapidly into a chamber which is maintained at a temperature that insures quick and complete vaporization of the sample.

The efficiency of the column determines the length of time it takes in order to perform an analysis. That is, a column of high efficiency can be of shorter length than a column of low efficiency and with the carrier gas flowing at the same rate, the analysis can be formed much more readily. It is, therefore, desirable to improve the efficiency of a column for two principal reasons; the first, is that a column of high efficiency can perform an analysis much more rapidly, and the second being that a column with high efficiency of an equivalent length compared to a column of standard efficiency will have greater resolution or the ability to measure the relative separation of two sample components and hence the capability of analyzing products, more precisely.

Efficiency of chromatographic columns is expressed in terms of theoretical plate height, which is simply a number of theoretical plates per unit of length necessary to effect resolution. As a component in a sample is moved through the column by a carrier gas, the velocity at which the component is travelling, the dimensions of the column, and the medium through which it travels will have a direct influence on column efficiency.

Eddy diffusion of the component around the column packing material and within the carrier gas will result in a loss of efficiency. Therefore, in order to minimize diffusion, highly efficient packed columns require (1) a solid supportive small, uniform particle size having high surface area or liquid phases of low viscosity on maximum loading; (2) column dimensions of longest practical length and smallest practical diameter, and (3) operation at the optimum flow rate of the carrier gas. Assuming that the carrier gas is injected at the optimum flow rate, the type of packing and column dimensions are the critical criteria for obtaining high efficiency.

Normally, chromatographic columns are made of either glass or metal tubing of convenient length and diameter. Glass has a principal advantage over metal primarily in its non-reactiveness with any of the components which may be used either in the mobile or immobile phases. Glass columns have generally been manufactured of capillary tubing having internal diameters of from 0.25mm to larger than 1mm with outside diameters from 4mm to 6mm. Because of the nature of the glass tubing to be used and fabricated, it is extremely difficult to fabricate columns of lengths greater than 25 feet. The possibility of inadvertent scratching or abrasion of a small section of the capillary tubing, as well as the combination of thermal change and vibrational stresses induced upon the column increase the possibilities of fracture. Therefore, while it is desirable to have columns as long as 200 feet manufactured of glass of small diameter tubing so as to increase the efficiency of the column, or simply, or more durable column, it has been nearly impossible to fabricate such a glass column.

This invention relates to a technique for fabricating such a glass column and to the resultant column with the attendant results of increasing efficiency in such columns from a conventional 800 plates per foot to in excess of 2000 plates per foot.

SUMMARY OF THE INVENTION

In accordance with one form of the invention, the chromatographic column consists of a monolithic glass cylinder having a pair of opposed surfaces and a side wall in which a continuous helical passageway is formed. The passageway is packed with gas absorptive material for performing the chromatographic process. Gas can be injected directly into the helical passageway and a pair of metal flanges can be inserted over the opposed surface comprising the top and bottom edges of the glass cylinder.

Quick-connect and disconnect couplings are provided on each flange to connect the column to suitable valve mechanisms for introducing the carrier gas into the passageway and to capture the effluent of the specimen for analysis.

The flanges can be formed from metal to preclude chipping and breaking of the monolithic glass construction and to further serve as a conductor to discharge static electricity which may adhere to the interior passageway in the monolithic structure. The couplings on the flange also provide a firm means of support for making the connections to the valve structure.

The monolithic glass construction may also take the form of a number of stacked plates fused together which have continuous interconnected passages of sinusoidal or other configuration formed therethrough. The passages are also packed with gas absorptive or adsorptive material.

By using such monolithic plates or cylinders, the height of the resulting column can be constructed at will with any diameter passage within practical limits, serving to effect a chromatographic column of high efficiency. Further, the resultant column because of its monolithic (or solid one piece) construction is extremely durable.

The cylindrical column can be formed by wrapping an expendable, sacrificial tubing in a coil or helix of appropriate spacing and length around a section of glass tubing supported on a mandrel. It is considered preferable to first cut, grind, etch or mold the glass tubing in the desired helical configuration or other desired configuration and to wrap the sacrificial tubing in the resulting grooved path to thereby establish and retain the desired spacing between the coils of tubing during subsequent processing. A second tube is then placed over the coil so a concentric sandwich is formed on the mandrel. Sufficient heat is applied to one end of the inner and outer tubes to effect fusing of the tubes at said one end thereof. A vacuum is drawn between the inner and outer tubes and heat is applied to the tubes, causing said tubes to flow into the interspacial areas between the sacrificial tubing, thereby fusing the glass tubes together and forming a monolithic structure. When this operation is complete, the sacrificial tubing is removed by means of an etchant or other reactant chemical compound such as $FeCl_3$, HCl, an acetic acid-nitric acid mixture and the like which creates a continuous passageway of the desired configuration through the monolithic structure. The resultant column is monolithic (or solid one piece) in structure having the integrity of a single heavy wall glass tube. The continuous passageway is then loaded with chromatographic packing thereby forming a monolithic packed chromatographic column.

In the stacked plate construction, sacrificial tubing may be placed in grooves cut, ground, etched or molded in a desired continuous passageway configuration on one of the two opposing surfaces of a glass plate and a second plate fused thereto. After removal of the sacrificial tubing, a monolithic plate having a continuous passageway formed therein is obtained. A plurality of such monolithic plates may be stacked one on top of the other with the outlet of one joined to the inlet of the next adjacent plate such as with a glass or metal U tube. The resulting continuous passageway through the stack of monolithic plates can be packed with chromatographic packing material to create a packed chromatographic column of significant strength and resistance to breakage. Moreover, a column obtained in this fashion is surprisingly compact and efficient.

BRIEF DESCRIPTION OF THE DRAWING

Further objects and advantages of the invention will become apparent from the following description and claims, and from the accompanying drawing, wherein:

FIG. 1 is top plan view, partly in section, of one form of a chromatographic column of the present invention;

FIG. 2 is a side view in elevation, partly in section, of the chromatographic column of FIG. 1;

FIG. 3 is a perspective view of the chromatographic column of FIGS. 1 and 2;

FIG. 4 is a top plan view, partly in section of another form of chromatographic column of the present invention;

FIG. 5 is a side view in elevation of the chromatographic column of FIG. 4;

FIG. 6 is a perspective view of the chromatographic column illustrated in FIGS. 4 and 5;

FIG. 7 is a side view in elevation, partly in secton, of still another form of chromatographic column in accordance with the present invention, and particularly, a chromatographic column having quick-connect and disconnect couplings and protective flanges;

FIG. 8 is a side view in elevation of the chromatographic column of FIG. 7 as seen from the right hand side of FIG. 7;

FIG. 9 is a cross-sectional view taken substantially along the plane indicated by line 9—9 of FIG. 7; and FIG. 10 is a perspective view of a portion of still another form of chromatographic column which can be constructed in accordance with the principles of the present invention.

DETAILED DESCRIPTION OF THE PREFERRED EMBODIMENTS

Referring now to the drawings in detail, wherein like numerals indicate like elements throughout the several views, one form of chromatographic column 10 constructed in accordance with the principles of the present invention is illustrated in FIGS. 1 to 3, inclusive.

Column 10 includes a monolithic glass cylindrical tube 12 having a helical passageway 14 formed in a side wall 16 thereof. One end of passageway 14 opens at 15 in the bottom edge 18 of cylinder 12 and the other end of passageway 14 has an opening 20 in the top edge 22 of cylinder 12.

Passageway 14 may be packed with a suitable packing material to effect separation of an entrained volatile sample in the carrier gas which is fed through one end of passageway 14 and exits through the other end of passageway 14 in cylinder 12. As discussed above, the components of the sample under analysis are selectively adsorbed and desorbed by the packing in passageway 14 and egress at different rates in a continuous stream from one end 15 or 20 of the passageway 14 wherein it can be analyzed as to its component parts.

Because of the nature of the monolithic construction of column 10, durable columns as long as 200 feet or more may be manufactured having a small diameter passageway 14 whereby the efficiency of the column may be substantially increased. For example, columns having more than 2,000 theoretical plates per foot have been fabricated with the construction illustrated in FIGS. 1 to 3 wherein heretofore it was only possible to fabricate columns of about 800 theoretical plates per foot.

Column 10 is fabricated in a monolithic construction by wrapping an expendable, sacrificial tubing in a helix of a length and width spacing between the coils of the helix as desired around an inner glass tubing section supported on a mandrel. It is considered preferable to cut, grind, etch or mold a grooved path on the outer surface of the inner glass tubing to serve as a guide and retainer for the sacrificial tubing. In this manner, the spacing between the wire can be preset and retained during the heating operation. A second outer section of glass tubing is placed over the coil and first tube to form a concentric sandwich on the supporting mandrel. Sufficient heat is applied to one end of the sandwich to effect fusing of the glass tubes at said one end thereof. A vacuum is then drawn between the inner and outer glass tubing to fuse and flow into the interspacial areas between the sacrificial tubing. When this operation is complete, the sacrificial tubing is removed by means of an acid etchant or other reactant compound which leaves the desired configuration for the column. A chromatographically chemically inert porous retainer is inserted into a terminal portion of the continuous passageway through the column to prevent loss of the packing material. Such retainers can be formed of fiber glass, glass wool, glass frits, an inert metal fiber or wool such as gold wool and the like. Such retainers can also be interposed in the terminal portion of the inlet and outlet lines leading to and from the column to further protect against loss of packing material. The passageway thus formed by removal of the sacrificial tubing is packed with an appropriate adsorption-desorption material and a porous retainer as described hereinabove can be inserted into the initial portion of the continuous passageway of the column thereby sealing the packing within the passageway of the column. The resultant structure is monolithic in nature having the integrity of a single heavy wall glass tube of desired length. Moreover, the precision bore of the passageway obtained through use of the sacrificial tubing is believed to help in obtaining packing uniformity.

As shown in FIGS. 7 to 9, inclusive, an annular metal flange 24 may be seated on the bottom and top edges 18 and 22 of cylindrical column 12, respectively. The metal flanges 24 preclude chipping of the monolithic glass construction of column 12 and can also serve to aid in the elimination of static charges carred by the sample under analysis in passageway 14.

Further, a first cylindrical coupling member 26 having a bayonet slot 28 can be integrally connect to each flange 24 over the inlet and outlet of passageway 14. Bayonet slots 28 receive a pin 30 attached to the side wall of a second spring loaded coupling member 32.

Coupling member 32 includes an inner sleeve 34 having a passageway 36 adapted to be placed over the ingress or egress of passageway 14 and aligned therewith. Inner sleeve 34 has an intermediate sleeve 36 fixed thereto. An annular flange 38 is formed intermediate the ends of intermediate sleeve 36 to hold a coil spring 40 captive between flange 38 and a cap 42 having a knurled outer surface. Cap 42 is fixed to the upper end of an outer cylindrical sleeve 44 mounting the pin 30 on opposite diametrical portions thereof, which is slidable relative to sleeves 34 and 36.

Coupling member 32 and pin 30 are inserted in the interior of the complemental cylindrical coupling member 26 with pin 30 in slot 28. When outer sleeve 44 is pushed downwardly into cylindrical coupling 26 and the pin 30 rotated into the horizontal portion of slot 28, coil spring 40 will be compressed, as outer sleeve 44 and cap 42 moves downwardly relative to intermediate sleeve 36 and inner sleeve 34.

The compressed spring 40 will be locked in compression as pin 30 is rotated into the horizontal portion of slot 28, exerting a force on pin 30 to lock the coupling 32 solidly in place within mating cylindrical coupling 26 with the bore 37 in sleeve 36 aligned with the corresponding end of passageway 14 in cylinder 12. In this manner, the chromatographic column 10 can be quickly connected and disconnected to suitable valves admitting the components of the sample under analysis issuing from the outlet of passageway 14 for analysis and connecting the sample in the inlet of passageway 14.

As shown in FIGS. 4 to 6, inclusive, the chromatographic column 10 can be formed with both the inlet and outlet for the gas sample in either the top or bottom edges 18 or 22 of the glass monolithic cylinder 12. As shown, the inlet 15 and outlet 20 can be disposed on opposite diametrical portions of the top edge 22 of cylinder 12. A flange 24 can be disposed over the top edge as well as the bottom edge, with a quick-disconnect and connect cylindrical coupling 26 over each of the inlet 15 and outlet 20. Accordingly, this monolithic construction of chromatographic tube 10 permits convenience for attachment for suitable analysis equipment.

With reference to FIG. 10, it will be apparent that the chromatographic column need not be in cylindrical form, but may comprise a plurality of substantially planar plates 50 stacked one above the other. Plates 50 include opposed planar surfaces 52 and 54 provided with an inlet 55 and outlet 56 of a continuous passageway 58 filled with suitable packing material. The passageway can be formed if any desired continuous configuration, e.g. sinusoidal and the like. The plates 50 can be stacked to any suitable height with the outlet of one plate being connected to the inlet of the next adjacent plate. Alternatively, the inlet 55 and the outlet 56 can be formed to emerge in adjacent surfaces 52 and 54 so that when plates are stacked, the inlets and outlets are in abutment. In either configuration, the plates can be fused together forming a continuous passageway through the stacked plates.

Each of the plates 50 may be formed as described heretofore using the same technique. A first substantially planar glass plate supported on a planar mandrel can have sacrificial tubing laid in grooves cut, ground, etched or molded in any desired configuration, in one of its planar surfaces. A second plate is then placed over the tubing, heating of the plates at one end thereof effects a seal and then a vacuum is drawn between the plates and the plates are further heated to fuse together. Thereafter, the sacrificial tubing is etched from the concentric sandwich. In the embodiment wherein the inlet and outlet emerge through opposed surfaces of the plates, a hole may then be drilled through each surface 52 and 54 to form the inlet and outlet for passageway 58.

The glass employed in the manufacture of the column of the present invention can be any glass which possesses a high coefficient of expansion. Typical glasses which can be employed are borosilicates and soda, lime glass, with borosilicate glasses being preferred. Especially preferred are the Kovar sealing type glasses such as types 7050, 7052 available from Corning Glass Works, Corning, New York, EN1 available from Owens Illinois, Toledo, Ohio, 706 available from General Electric, Schenectady, New York and the like.

Metals which can be employed for the sacrificial tubing and the metal flanges which can be fused to the glass column are metals whose coefficients of expansion match those of the glass employed for the column. Thus, Kovar, an iron-nickel-cobalt alloy, available from the Carpenter Steel Company of Bridgeport, Connecticut is especially suitable for use with borosilicate glasses. Similarly, Sylvania No. 4 is an iron-nickel-cobalt alloy availabe from Sylvania of Danvers, Massachusetts.

While specific embodiments of a chromatographic column have been disclosed in the foregoing description, it will be understood that varvious modifications within the spirit of the invention may occur to those skilled in the art. Therefore, it is intended that no limitations be placed on the invention except as defined by the scope of the appended claims.

What is claimed as new is:

1. A packed chromatographic column comprising a glass monolithic construction having at least one pair of opposed surfaces and solid glass therebetween;

A continuous passageway of essentially constant diameter adapted to receive a fluid therethrough contained wholly within said solid glass between said opposed surfaces of said monolithic contruction, the passageway having an inlet and an outlet opening in at least one of said opposed surfaces, and chromatographic packing material in said passageway for separating the components of a fluid sample introduced into and flowing through said passageway from said inlet to said outlet.

2. The packed chromatographic column of claim 1 wherein said inlet to said continuous passageway is in one of said opposed surfaces and the outlet of said continuous passageway is in the other of said opposed surfaces.

3. The packed chromatographic column of claim 2 wherein said glass monolithic construction is the side wall of a cylindrical tube, said side wall containing said continuous passageway.

4. The packed chromatographic column of claim 3 wherein said continuous passageway is in the form of a helix wound in said side wall.

5. The packed chromatographic column of claim 4 wherein
   said opposed surfaces include a top and bottom edge of said cylinder, and
   said helical passageway has an inlet in one of said edges of said cylinder and an outlet in the other of said edges of said cylinder.

6. The packed chromatographic column of claim 5 including
   means mounted on said top and bottom edges of said cylinder for coupling said inlet and outlet of said helical passageway to an analysis device.

7. The packed chromatographic column of claim 6 wherein said coupling means includes
   an annular flange positioned on the top and bottom edge of said cylinder over said inlet and outlet,
   a first cylindrical coupling member fixed to each of said flanges over said inlet and outlet, and
   a second coupling member removable connectable to each of said first coupling members having a passageway therethrough in communication with said inlet and outlet.

8. The packed chromatographic column of claim 7 wherein said first coupling member includes
   a bayonet-type slot, and
   said second coupling member includes
   at least one pin extending from a side wall thereof received within said bayonet-type slot on said first coupling member.

9. The packed chromatographic column of claim 8 wherein said second coupling member includes
   means for locking said pin and second coupling member to said first coupling member.

10. The packed chromatographic column claim 9 wherein said locking means includes
    spring means in said second coupling member for retaining said pin within said bayonet type slot on said first coupling member.

11. The packed chromatographic column of claim 1 wherein said glass monolithic construction includes at least one substantially planar plate.

12. The packed chromatographic column of claim 11 including
    a plurality of stacked planar plates fused together,
    each having a continuous passageway therethrough contained wholly within each plate in communication with a passageway of an adjacent plate.

13. The packed chromatographic column of claim 11 wherein
    said continuous passageway is sinsoidal in shape.

14. The packed chromatographic column of claim 12 wherein said continuous passageway has an inlet in one of said opposed surfaces and an outlet in the other of said opposed surfaces of each of said plates.

15. The packed chromatographic column of claim 1 wherein said inlet and outlet of said continuous passageway is in one of said apposed surfaces.

16. The packed chromatographic column of claim 15 wherein said glass monolithic construction is the side wall of a cylindrical tube, said side wall containing said continuous passageway.

17. The packed chromatographic column of claim 16 wherein
    said opposed surfaces include a top and bottom edge of said cylinder and
    said continuous passageway has an inlet and outlet in one of said edges of said cylinder.

18. The packed chromatographic column of claim 17 including
    means mounted on said one edge of said cylinder for coupling said inlet and outlet of said helical passageway to an analysis device.

19. The packed chromatographic column of claim 18 wherein said coupling means includes
    an annular flange positioned on said one edge of said cylinder over said inlet and outlet,
    a first cylindrical coupling member fixed to each of said flanges over said inlet and outlet, and
    a second coupling member removable connectable to each of said first coupling members having a passageway therethrough a communication with said inlet and outlet.

20. The packed chromatographic column of claim 19 wherein said first coupling member inclues
    a bayonet-type slot, and
    said second coupling member includes
    at least one pin extending from a side wall thereof received within said bayonet-type slot on said first coupling member.

21. The packed chromatographic column of claim 20 wherein said second coupling member includes
means for locking said pin and second coupling member to said first coupling member.

22. The packed chromatographic column of claim 21 wherein said locking means includes
spring means in said second coupling member for retaining said pin within said bayonet type slot on said first coupling member.

* * * * *